United States Patent
Aphkhazava (10) Patent No.: US 10,352,939 B2
(45) Date of Patent: Jul. 16, 2019

(54) SIMULTANEOUS MEASUREMENT OF HALIDE ION CONCENTRATION AND PH

(71) Applicant: David Aphkhazava, Tbilisi (GE)

(72) Inventor: David Aphkhazava, Tbilisi (GE)

( * ) Notice: Subject to any disclaimer, the term of this patent is extended or adjusted under 35 U.S.C. 154(b) by 220 days.

(21) Appl. No.: 15/494,837

(22) Filed: Apr. 24, 2017

(65) Prior Publication Data

US 2018/0306777 A1    Oct. 25, 2018

(51) Int. Cl.
*G01N 33/58* (2006.01)
*C07K 14/00* (2006.01)
*G01N 33/542* (2006.01)
*G01N 33/84* (2006.01)

(52) U.S. Cl.
CPC .......... *G01N 33/582* (2013.01); *C07K 14/00* (2013.01); *G01N 33/542* (2013.01); *G01N 33/84* (2013.01)

(58) Field of Classification Search
None
See application file for complete search history.

(56) References Cited

FOREIGN PATENT DOCUMENTS

EP    1514922 A1 *   3/2005   .......... C07K 14/405

* cited by examiner

*Primary Examiner* — Kagnew H Gebreyesus
(74) *Attorney, Agent, or Firm* — Hoffman Warnick LLC

(57) ABSTRACT

Embodiments of the invention relate to the quantitative measurement of halide ion concentration and pH using novel fluorescent polypeptides. One embodiment of the invention provides a polypeptide containing at least one amino acid sequence selected from a group consisting of: Sequence ID No. 3, Sequence ID No. 4, Sequence ID No. 5, and Sequence ID No. 6.

7 Claims, 7 Drawing Sheets

Specification includes a Sequence Listing.

SIMULTANEOUS MEASUREMENT OF HALIDE ION CONCENTRATION AND PH

SEQUENCE LISTING

The sequence listing contained in the electronic file titled "ILIA-0001_SEQUENCE_LISTING_ST25.txt," created 24 Apr. 2017, comprising 13 KB, is hereby incorporated herein.

BACKGROUND

Fluorescent proteins have been employed for various purposes in the past, including the measurement of pH and halide ion concentration. The available halide-sensitive fluorescent proteins, however, have been found to be highly pH-dependent, making detection of ions inaccurate upon even slight variations in pH. What is more, known techniques employing fluorescent proteins for pH measurement or halide ion concentration measurement are time-intensive.

SUMMARY

Embodiments of the invention relate generally to fluorescence detection and, more particularly, to simultaneous, quantitative measurement of pH and halide ion concentration using fluorescence detection.

In one embodiment, the invention provides a polypeptide containing at least one amino acid sequence selected from a group consisting of: Sequence ID No. 3, Sequence ID No. 4, Sequence ID No. 5, and Sequence ID No. 6. In some embodiments, the polypeptide includes Sequence ID No. 5 and Sequence ID No. 6.

In another embodiment, the invention provides a nucleic acid molecule comprising a nucleotide sequence coding for a polypeptide including at least one amino acid sequence selected from a group consisting of: Sequence ID No. 3, Sequence ID No. 4, Sequence ID No. 5, and Sequence ID No. 6. In some embodiments, the nucleic acid molecule includes nucleotide sequences coding for the polypeptide of Sequence ID No. 5 and the polypeptide of Sequence ID No. 6.

In yet another embodiment, the invention provides a method of simultaneously measuring a halide ion concentration and pH in a living cell, the method comprising: imparting light having a wavelength of about 450 nm onto a cell containing polypeptide including the amino acid sequence of Sequence ID No. 5 and the amino acid sequence of Sequence ID No. 6; and measuring light emitted from the polypeptide in response to absorbing the imparted light, wherein an intensity of the light emitted from the polypeptide is indicative of the halide concentration of the cell and the pH of the cell.

In still another embodiment, the invention provides an assay comprising: a substrate; and a polypeptide within or atop the substrate, the polypeptide including at least one amino acid sequence selected from a group consisting of: Sequence ID No. 3, Sequence ID No. 4, Sequence ID No. 5, and Sequence ID No. 6.

In still yet another embodiment, the invention provides a host cell containing a polypeptide containing at least one amino acid sequence selected from a group consisting of: Sequence ID No. 3, Sequence ID No. 4, Sequence ID No. 5, and Sequence ID No. 6. In some embodiments of the invention, the host cell contains a polypeptide containing the amino acid sequence of Sequence ID No. 5 and the amino acid sequence of Sequence ID No. 6.

BRIEF DESCRIPTION OF THE DRAWINGS

These and other features of the invention will be more readily understood from the following detailed description of the various aspects of the invention taken in conjunction with the accompanying drawings that depict various embodiments of the invention, in which.

It is noted that the drawings are not to scale. The drawings are intended to depict only typical aspects of the invention and therefore should not be considered as limiting the scope of the invention. In the drawings, like numbering represents like elements between and among the drawings.

DETAILED DESCRIPTION

As used herein, a "coding sequence" is a polynucleotide sequence which is translated into a polypeptide.

The term "plasmid" refers to a circular, double-stranded unit of DNA capable of replication independent of chromosomal DNA and suitable for use as a vector for gene insertion into a cell via, for example, transfection.

The term "polynucleotide" as used herein refers to a polymeric form of nucleotides of any length, either ribonucleotides or deoxyribonucleotides, whether single- or double-stranded.

The term "polypeptide" refers to a polymer of amino acids of any length and therefore includes peptides, oligopeptides, and proteins. The term also refers to polymers of amino acids that have undergone subsequent modification, such as, for example, glycosylation, phosphorylation, or acetylation.

Various methods according to the invention include the use of a plasmid containing a DNA sequence encoding a polypeptide under the control of regulatory sequences directing expression of the plasmid DNA. One skilled in the art will understand that such regulatory sequences include, for example, promoter and enhancer sequences, polyadenylation sequences, an origin of replication (ori) sequence, and restriction sites. Uses of such a plasmid include the introduction of the plasmid into a cell, referred to herein as "transfection" (in the case of eukaryotic cells) or "transformation" (in the case of bacterial cells). Such introduction may be accomplished by any number of methods, including, without limitation, electroporation, liposome transfection, chemical transfection, or microinjection.

An ideal biosensor is one that can monitor analyte concentration changes in realtime without artifacts. One shortcoming of the existing biosensors, however, is temporal resolution. That is, in many biological systems, and with most known biosensors, an analyte concentration changes faster than can be detected by the biosensor.

Applicant has developed a number of novel biosensors that exhibit superior properties, as compared to known biosensors. Specifically, Applicant has developed novel polypeptides for the measurement of halide ion concentration and pH. Unlike known methods, however, these novel polypeptides may be employed together to simultaneously measure pH and halide ion concentration in a host cell.

Novel Polypeptides for the Measurement of Halide Ion Concentration

The polypeptides of the invention useful for measuring halide ion concentration, and specifically chloride ion concentration, are novel mutations of the Yellow Fluorescent Protein (YFP) sequence, a known 239 amino acid (717 nucleotide) sequence. The YFP amino acid sequence is provided as Sequence ID No. 1 of the Sequence Listing. A known variant (YFP***) is provided as Sequence ID No. 2, and includes mutations at position 149 (histidine to glutamine), position 153 (isoleucine to leucine), and position 164 (valine to serine).

Applicant constructed a gene library in which the amino acids at positions 149, 153, and 164 of the YFP sequence were subjected to simultaneous site-specific mutagenesis. These positions were identified from the X-ray structure of YFP-H148Q. The sequences of the gene library were cloned into the expression vector pET23b and transformed into cells of the BL21(DE3) E. coli strain.

A first novel polypeptide, referred to as GEICS1.1 (Genetically-Encoded Intensiometric Chloride Sensor) (Sequence ID No. 3) includes mutations at position 149 (histidine to methionine) and position 164 (valine to serine).

A second novel polypeptide, referred to as GEICS1.2 (Sequence ID No. 4) includes mutations at position 149 (histidine to leucine) and position 164 (valine to serine).

A third novel polypeptide, referred to as GEICS1.3 (Sequence ID No. 5) includes mutations at position 149 (histidine to leucine), position 153 (isoleucine to leucine), and position 164 (valine to serine).

While each of these three novel polypeptides exhibited suitable halide sensitivity, the GEICS1.3 variant (Sequence ID No. 5) proved superior to either the GEICS1.1 variant (Sequence ID No. 3) or the GEICS1.2 variant (Sequence ID No. 4). Specifically, as will be explained in greater detail below, the GEICS1.3 variant exhibited superior chloride ion affinity and an improved association/dissociation rates. Therefore, in embodiments of the invention directed toward the measurement of halide ion concentration, the GEICS1.3 polypeptide is preferred.

Novel Polypeptide for the Measurement of pH

The polypeptides of the invention useful in the measurement of pH include a novel mutation of the far-red fluorescent protein mNeptune. This novel mutation, LSSmNeptune1 (Sequence ID No. 6), includes a large Stokes shift (LSS) with mutations at amino acid positions 70, 153, 158, 173, and 194, as compared to mNeptune. As will be explained in greater detail below, the LSSmNeptune1 polypeptide proved capable of reporting absolute values of intracellular pH in the range of 4-10.

GEICS1.3-LSSmNeptune1 Polypeptide

Figure 1:
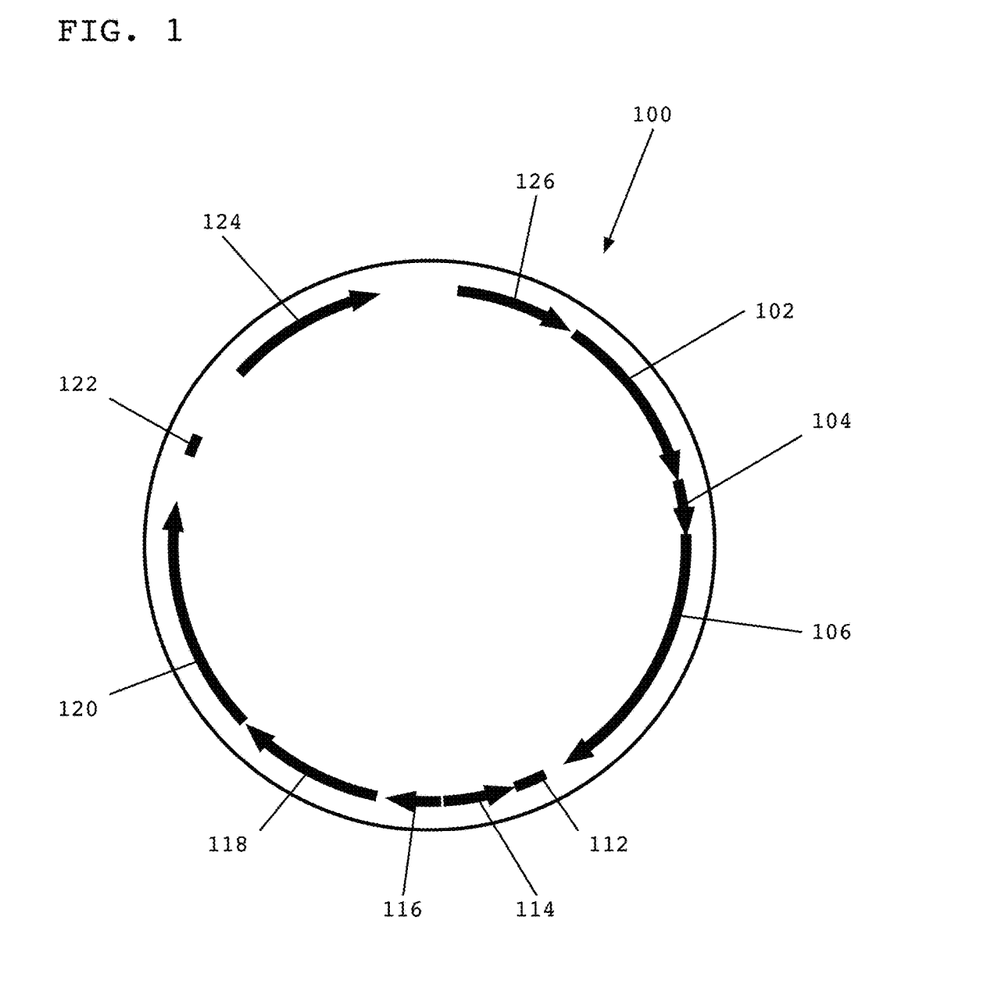
FIG. 1 shows a schematic representation of a plasmid including nucleotide sequences for both the GEICS1.3 and LSSmNeptune1 polypeptides, according to an embodiment of the invention.

Referring now to the drawings, FIG. 1 shows a schematic representation of a plasmid 100 according to one embodiment of the invention. Plasmid 100 includes nucleotide sequences coding for the GEICS1.3 sequence 102, the LSSmNeptune1 sequence 106, and a linker sequence 104 therebetween.

Linker sequence 104 may consist, according to various embodiments of the invention, of a 17-amino acid sequence or a 26-amino acid sequence. In practice, Applicant has found the 26-amino acid sequence to be preferred.

As will be recognized by one skilled in the art, plasmid 100 may include various other sequences, including, for example, polyadenylation sequences 112, 122, origination sequences 114, 124, promoter sequences 116, 118, 126, and sequences 120 coding for various enzymes, such as neomycin-kanamycin phosphotransferase. The functions of such sequences will be apparent to one skilled in the art and are not further described herein.

Figure 2:
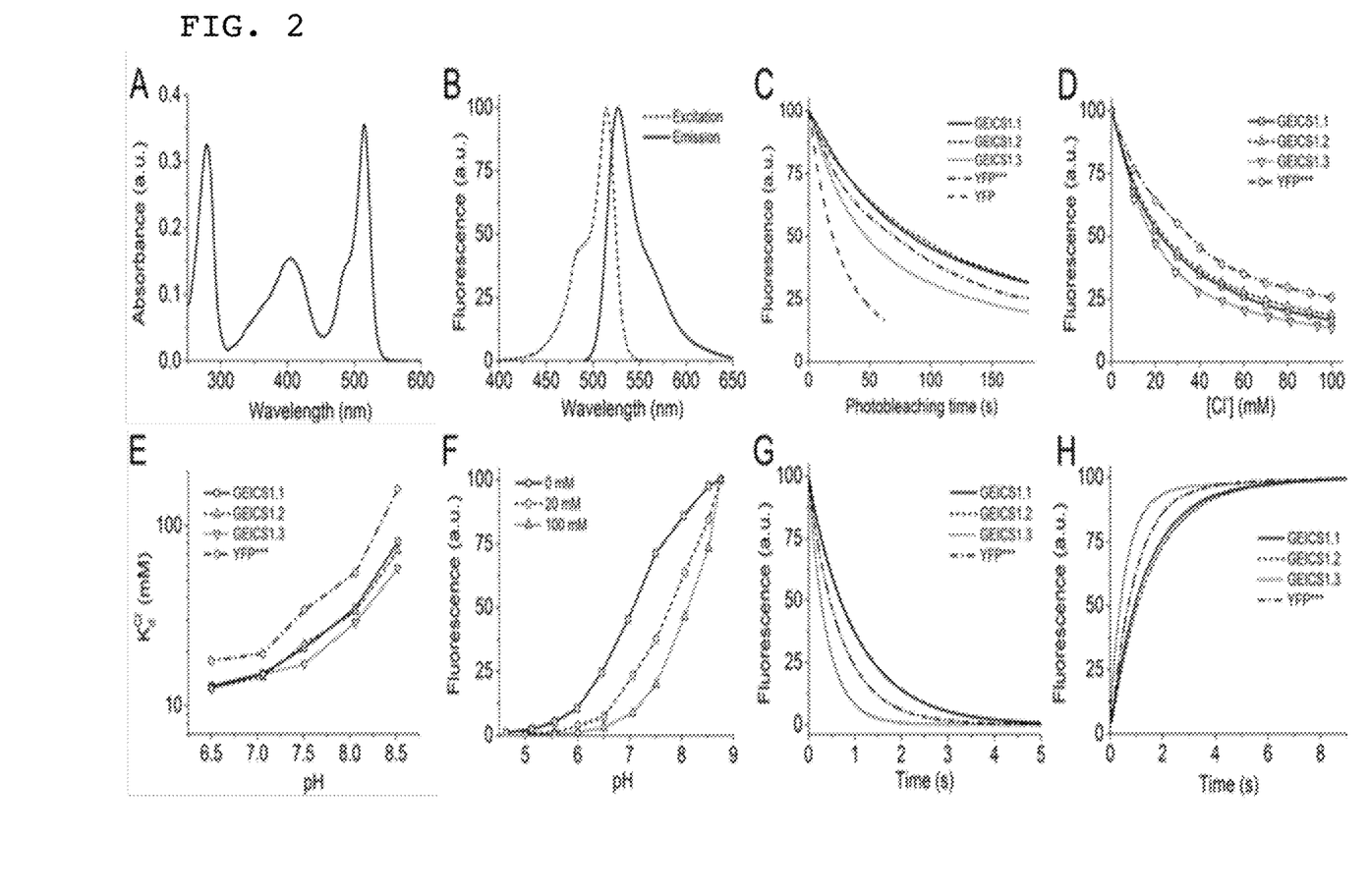
FIG. 2 shows spectra and curves showing various photochemical and biochemical properties of the GEICS sequence variants according to embodiments of the invention.

FIG. 2 shows spectra and curves of various photochemical and biochemical properties of the GEICS variants, including GEICS1.3. Panel A shows the absorbance spectrum of GEICS1.3 at pH 7.4 and 0 mm Cl⁻. Panel B shows the normalized fluorescence excitation (solid line) and emission (broken line) spectra of GEICS1.3. Panel C shows normalized curves of photobleaching under continuous 488 mm laser illumination for GEICS1.1, GEICS1.2, GEICS1.3, YFP*, and YFP. Panel D show the titration of the three GEICS variants and YFP* to Cl⁻ at pH 7.4.

Panel E of FIG. 2 shows the dependence of Cl⁻ affinities ($K_d$) for the GEICS variants and YFP*** on pH. Panel F shows fluorescence pH titrations of GEICS1.3 at Cl⁻ concentrations of 0 mM, 20 mM, and 100 mM.

Panel G shows normalized curves for the Cl⁻ association kinetics of the GEICS variants and YFP*, measured by stopped-flow fluorimentry. In panel G, the GEICS1.1 and GEICS1.2 curves are identical and appear as a single solid line. Panel H shows normalized curves for Cl⁻ dissociation kinetics of the GEICS variants and YFP*, again measured by stopped-flow fluorimentry.

Various fluorescence properties of the GEICS variants are summarized below in Tables 1 and 2 with reference to YFP, YFP***, and the green fluorescent protein (GFP) mutant E²GFP.

TABLE 1

| Protein/ mutations | Abs/Em max (nm) | Extinction coefficient, $M^{-1}cm^{-1}$ | Quantum yield | Relative brightness | pH stability |
|---|---|---|---|---|---|
| YFP | 514/527 | 83 400 | 0.61 | 1 | 4.81 |
| E²GFP | 514/524 | 25 000 | 0.69 | 0.34 | 6.81 |
| YFP*** | 514/527 | 30 900 | 0.59 | 0.36 | 7.23 |
| GEICS1.1 | 515/527 | 25 400 | 0.65 | 0.33 | 7.05 |
| GEICS1.2 | 515/527 | 27 000 | 0.62 | 0.33 | 6.97 |
| GEICS1.3 | 515/527 | 24 700 | 0.62 | 0.30 | 7.03 |

TABLE 2

| Protein/ mutations | Photostability under laser illumination 488 nm, s | $K_d$Cl, mM | YFP-chloride association kinetics, ms |
|---|---|---|---|
| YFP | 19 | 806 | ND |
| E²GFP | ND | 55 | 2500 |
| YFP*** | 69 | 34 | 460 |
| GEICS1.1 | 84 | 21 | 700 |
| GEICS1.2 | 88 | 22 | 680 |
| GEICS1.3 | 46 | 17 | 266 |

As can be seen from Tables 1 and 2, and FIG. 2, the GEICS variants possess similar spectral, biochemical, and photochemical properties. All GEICS variants exhibited fluorescence excitation/emission maxima at about 515/527 nm, similar to that of YFP. Photostability under 488 nm laser illumination was significantly higher than YFP for all GEICS variants (4.4-fold for GEICS1.1, 4.6-fold for GEICS1.2, and 2.3-fold for GEICS1.3).

Chloride anion association and dissociation kinetics of the GEICS variants, as compared to YFP*** and E²GFP are shown below in Table 3.

TABLE 3

| Protein | pH 7.4 | | pH 6.5 | |
|---|---|---|---|---|
| | $\tau_{1/2assoc}$ (ms) | $\tau_{1/2dissoc}$ (ms) | $\tau_{1/2assoc}$ (ms) | $\tau_{1/2dissoc}$ (ms) |
| E²GFP | 2470 ± 40 | ND | 1060 ± 20 | ND |
| YFP*** | 460 ± 40 | 686 ± 7 | 230 ± 8 | 320 ± 10 |
| GEICS1.1 | 686 ± 8 | 940 ± 70 | 310 ± 10 | 470 ± 20 |
| GEICS1.2 | 670 ± 10 | 1040 ± 50 | 297 ± 7 | 450 ± 30 |
| GEICS1.3 | 262 ± 4 | 380 ± 40 | 140 ± 30 | 187 ± 1 |

To assess the function of the GEICS variants in living cells, GEICS1.1, GEICS1.2, and GEICS1.3 mutant constructs were transiently transfected into Chinese hamster ovary (CHO) cells. A flux assay demonstrated that each GEICS variant fluoresced brightly when incubated in low-chloride media at 29° C. An increase in fluorescence was observed at 37° C. for each GEICS variant and was superior to that of YFP and YFP***.

Table 4 below shows anion sensitivities for each of the GEICS variants, as compared to YFP***, at pH 7.4 and constant ionic strength.

TABLE 4

| Protein | $K_d$ Cl, mM | $K_d$ I, mM | $K_d$ SCN, mM | $K_d$ Br, mM | $K_d$ NO$_3$, mM |
|---|---|---|---|---|---|
| YFP*** | 34 | 23 | 29 | 42 | 41 |
| GEICS1.1 | 21 | 54 | 23 | 44 | 38 |
| GEICS1.2 | 22 | 57 | 26 | 45 | 40 |
| GEICS1.3 | 17 | 16 | 19 | 29 | 29 |

Figure 3:
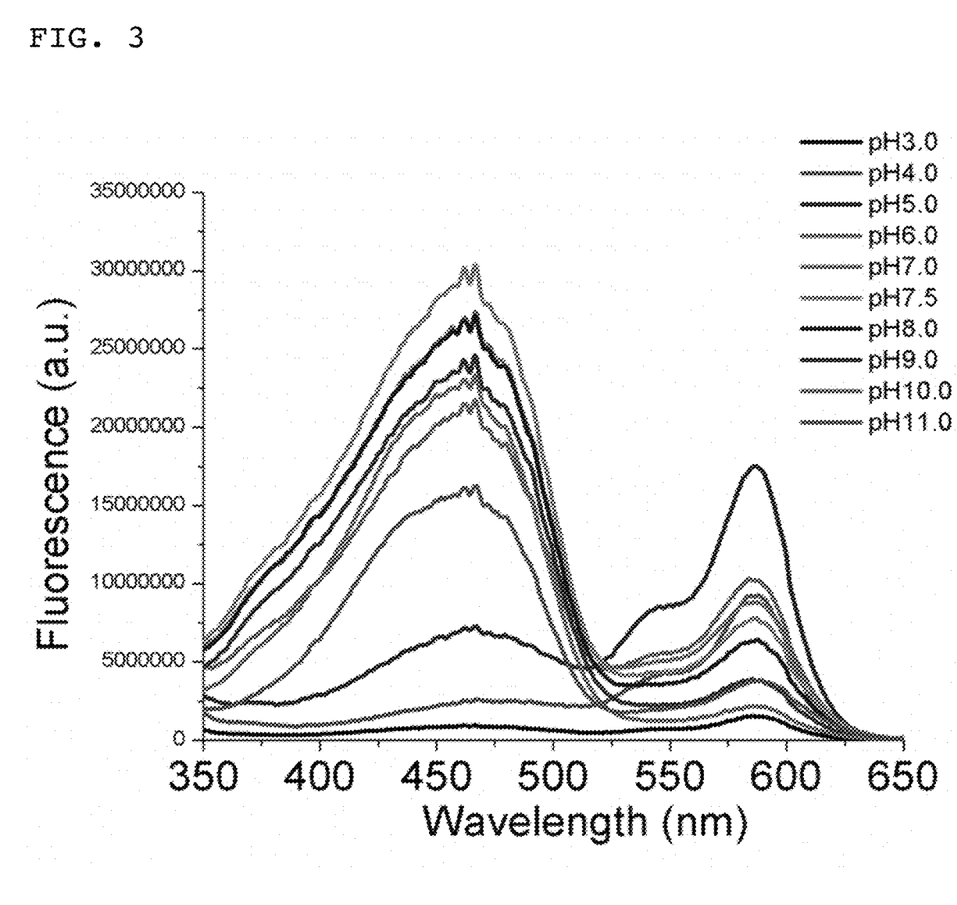
FIG. 3 shows emission spectra of the LSSmNeptune1 polypeptide according to an embodiment of the invention.

FIG. 3 shows absorbance spectra of LSSmNeptune1 as a function of pH. The highest emission was detected at pH 7.5 between 450 nm and 500 nm.

Figure 4:
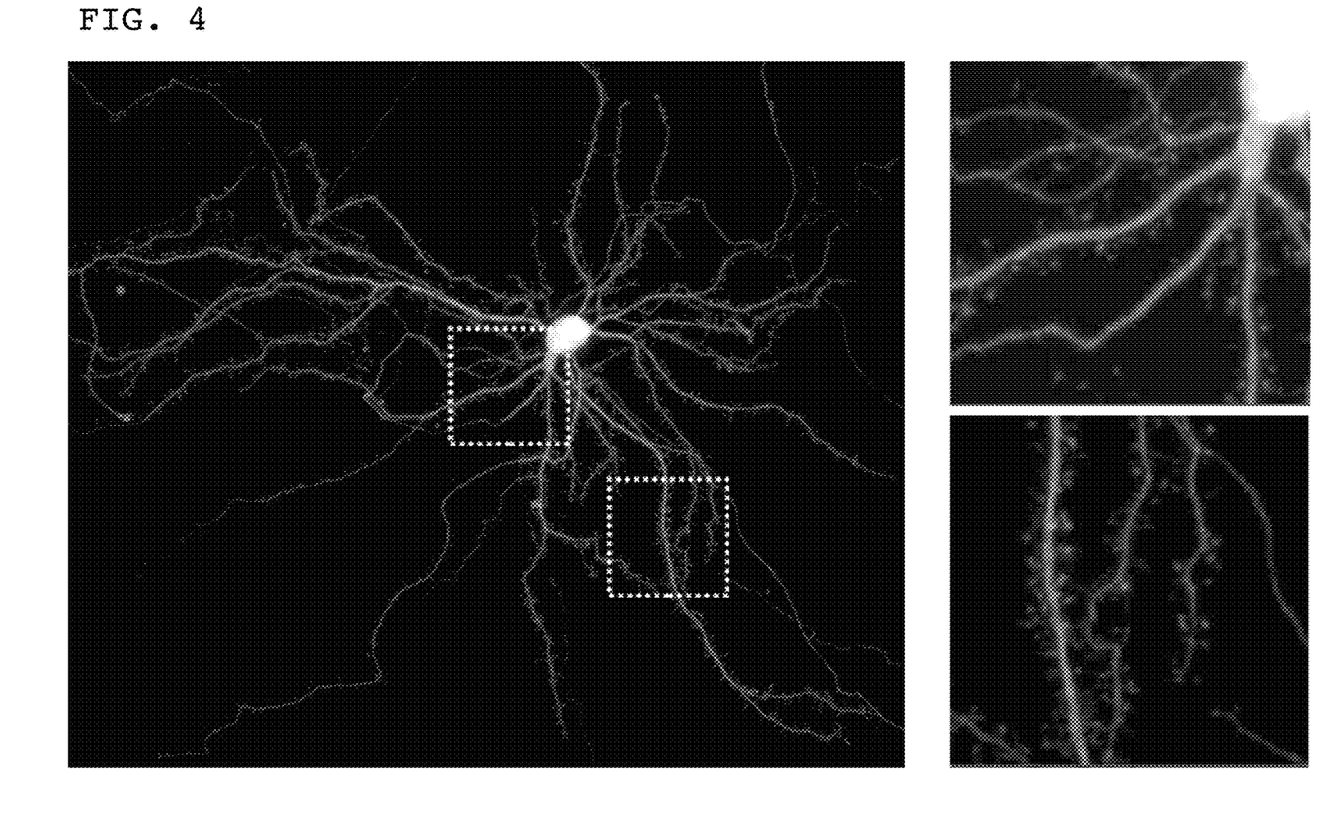
FIG. 4 shows photomicrographs of the fluorescence of the GEICS1.3 polypeptide within a hippocampal mouse neuron.

FIG. 4 shows photomicrographs of the fluorescence of the GEICS1.3 polypeptide within a primary hippocampal mouse neuron after 20 days in vitro, expressed under the control of the human synapsin promoter. The smaller inset photomicrographs show magnified views of the two boxed areas in the larger photomicrograph.

As can be seen in FIG. 4, the GEICS1.3 polypeptide is evenly distributed within the cell body, nucleus, and individual dendrites. No aggregation or non-specific localization of the polypeptide is present.

Figure 5:
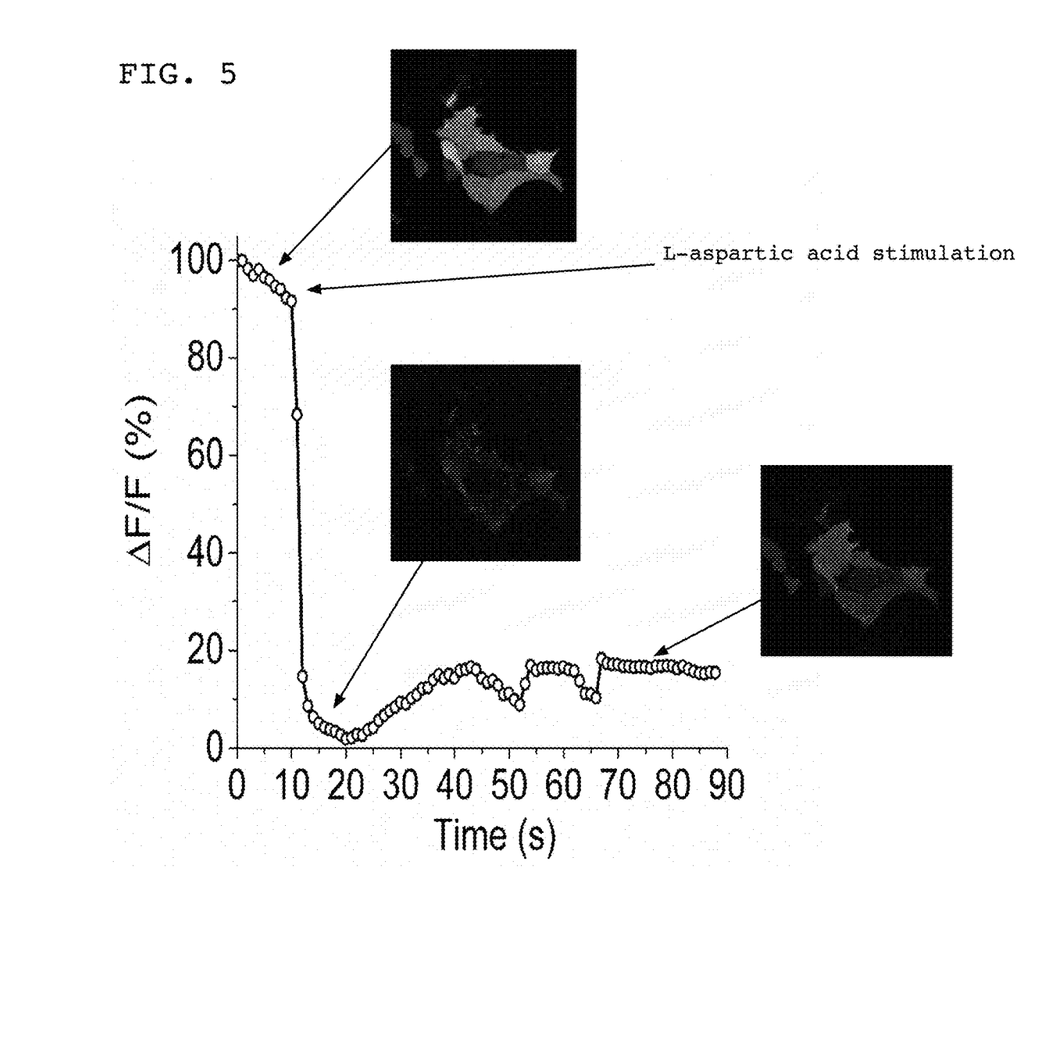
FIG. 5 shows a plot of GEICS1.3 fluorescence before, during, and after stimulation of chloride transport in human embryonic kidney (HEK) cells.

FIG. 5 shows a plot of GEICS1.3 fluorescence before, during, and after stimulation of chloride transport in human embryonic kidney (HEK) cells, along with inset photomicrographs at several timepoints. Prior to the stimulation of chloride transport with 1 mM L-aspartic acid, fluorescence of GEICS1.3 (green) is significant. Fusion of excitatory amino acid transporter 4 (EAAT4) with mCherry (red) is also visible. At 10 seconds following administration of L-aspartic acid, GEICS1.3 fluorescence is reduced to near zero. At 80 seconds following administration of L-aspartic acid, GEICS1.3 fluorescence has recovered to 10-20% of its original fluorescence as chloride transport wanes.

As noted above, a significant advantage of embodiments of the invention is the ability to simultaneously measure halide ion concentration using GEICS1.3 and pH using LSSmNeptune1.

Figure 6:
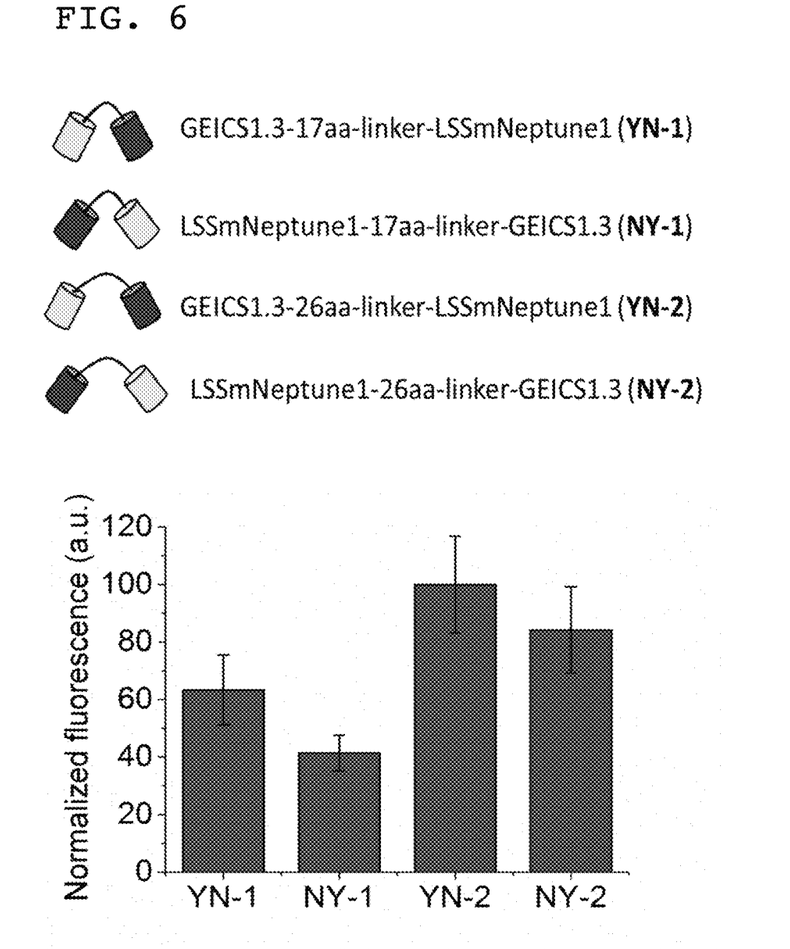
FIG. 6 shows a schematic representation of a GEICS1.3-LSSmNeptune1 polypeptide and corresponding fluorescence measures according to various embodiments of the invention.

FIG. 6 shows a schematic representation of the GEICS1.3-LSSmNeptune1 polypeptide according to various embodiments of the invention, as well as the normalized fluorescences of each. Fluorescence was measured in HEK293T cells 24 hours after transient transfection.

As can be seen, polypeptides employing a 26-amino acid linker sequence between the GEICS1.3 and LSSmNeptune1 sequences exhibited greater fluorescence, as compared to otherwise identical polypeptides employing a 17-amino acid linker sequence. The longer linker sequence is believed to facilitate better maturation of LSSmNeptune1. It was found that the actual amino acid sequence comprising the linker sequence was not of significance in either case, although the 26-amino acid sequence of Sequence ID No. 7 was found to be suitable in various embodiments of the invention.

As can also be seen in FIG. 6, irrespective of the linker sequence used, fluorescence was greater where the GEICS1.3 sequence was placed upstream of the LSSmNeptune1 sequence.

Figure 7:
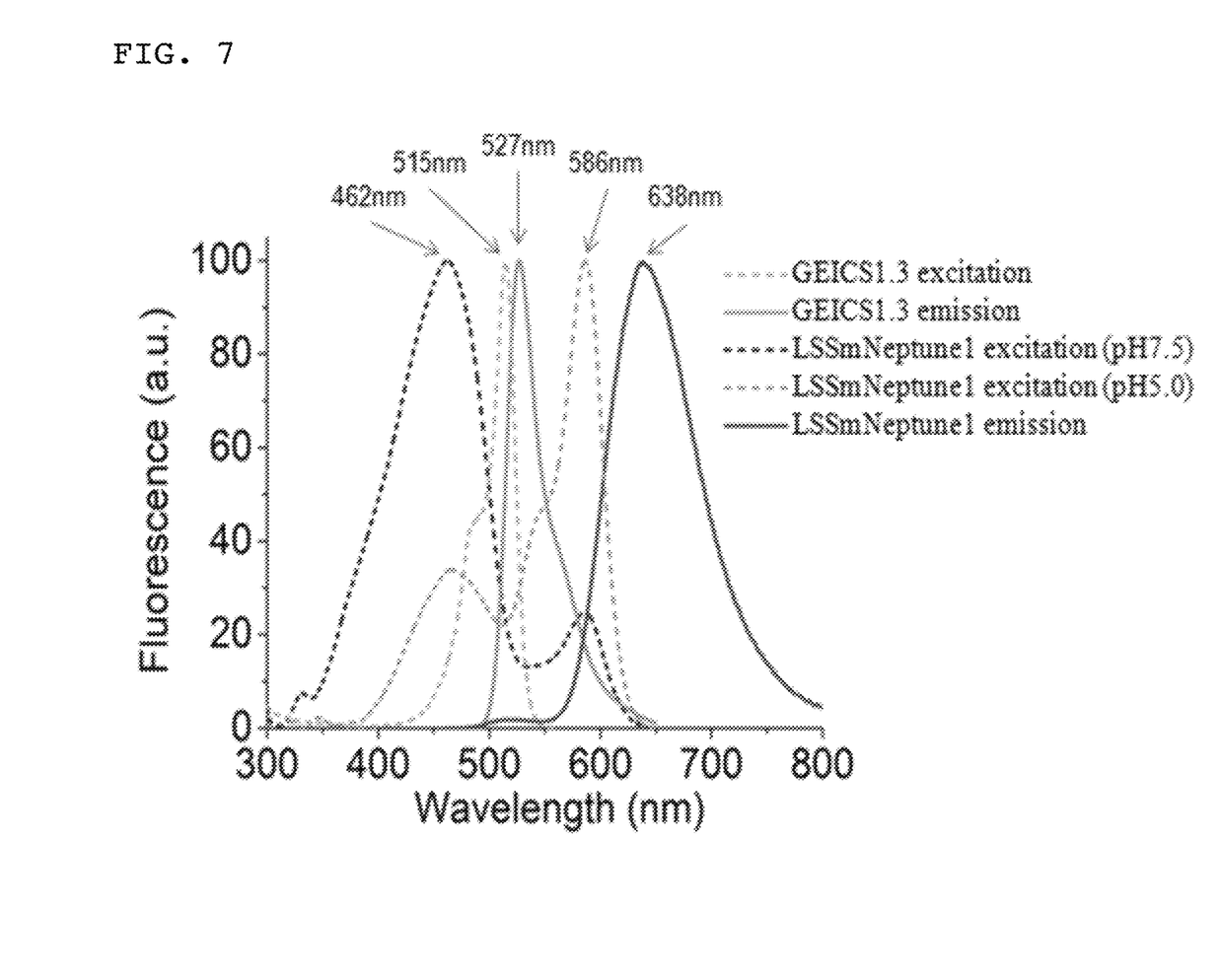
FIG. 7 shows normalized, simultaneously-obtained fluorescence spectra of GEICS1.3 and LSSmNeptune1 at pH 5.0 and pH 7.5.

FIG. 7 shows a plot of normalized simultaneous fluorescence spectra of the GEICS1.3 and LSSmNeptune1 polypeptides at pH 5.0 and pH 7.5. Excitation was accomplished using a 450 nm LED. The fluorescence spectra of GEICS1.3 and LSSmNeptune1 are resolvable, allowing for the independent imaging of each protein using standard filter sets. The data shown in FIG. 7 were obtained using two emission filters for each—530/40 BP for GEICS1.3 and 640/40 BP for LSSmNeptune1. For imaging the red form of LSSmNeptune1, a 590 nm LED was used for excitation and 640 LP for emission.

Table 5 below shows a comparison of the GEICS1.3-LSSmNeptune1 polypeptide (which is referred to therein as a Genetically Encoded Ratiometric pH and Halide (GERaph) sensor) with a known YFP***-derived sensor and a known E²GFP-derived sensor known as ClopHensor.

TABLE 5

| Property | Cl-sensor | ClopHensor | GERapH | Comments |
|---|---|---|---|---|
| Composition | YFP*** (Cl-sensitive yellow fluorescent protein derived from YFP) and CFP (cyan fluorescent protein), it is improved | E²GFP (Cl-sensitive derivative of EGFP, EGFP/T203Y), DsRed-monomer (monomeric version of DsRed, not pH sensitive) | GEICS1.3 (Cl-sensitive yellow fluorescent protein derived from YFP), LSSmNeptune (ratiometric red fluorescent pH-sensor, much brighter than the | GERapH design gives advantages in imaging procedure, simultaneous monitoring of pH and [Cl] requires only two excitation wavelength (455-490 nm and 560-580 nm) |

TABLE 5-continued

| Property | Cl-sensor | ClopHensor | GERapH | Comments |
|---|---|---|---|---|
| | variant of Clomeleon | | only one available red pH-sensor pHRed) | |
| Imaging technique | Widefield, confocal and two photon microscopy | Only confocal, cannot be used for two photon microscopy with conventional Ti-sapphire laser | Wide-field, confocal and two photon microscopy | Two photon technique is widely used for brain slice imaging |
| Imaging procedure | FRET-based ratiometric sensor, may require calibration prior imaging | Non-FRET ratiometric sensor, requires three excitation wavelengths, does not require callibration | Non-FRET ratiometric sensor, requires only two excitation wavelength, does not require calibration | FRET technique is not always easy to use, low SNR |
| Measured parameter | [Cl] can be reliably measured only with no changes in pH | [Cl] can be reliably measured in wide range of pH | [Cl] can be reliably measured in wide range of pH | Often intracellular changes in [Cl] is accompanied by noticeable changes in pH for at least 0.5 |
| Cl⁻ sensitivity | 35 mM | 55 mM | 17 mM | [Cl] in hippocampal slices 5-20 mM, in CHO cells 23 mM |
| Temporal resolution | 600 ms | 2500 ms | 266 ms | Changes in [Cl] are usually rapid |
| Brightness relative to YFP | 33% | 20% | 30% | High brightness better SNR |

Polypeptides according to various embodiments of the invention may be employed in any number of contexts. For example, they may be used in vivo for the measurement of ligand transport on the surface of a living cell or in vitro, where ligand efflux is measured in a cell culture.

Alternatively, a fluid extract from cells or tissues may be used as a sample from which ligands are detected or measured. With amino acid sensors such as glutamate sensors, such measurements may be used to detect extracellular glutamate associated with traumatic injury to neurons or as a possible indicator of a neurological disorder associated with glutamate excitotoxicity, including, for example, stroke, epilepsy, Huntington disease, AIDS, dementia complex, and amyotrophic lateral sclerosis.

Polypeptides according to various embodiments of the invention may also be used in high-throughput and high-content drug screening. For example, a solid support or multi-well dish comprising polypeptides according to the invention may be used to screen multiple potential drug candidates simultaneously. As such, polypeptides according to the invention are useful in methods of identifying compounds that modulate binding of a ligand to a receptor.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A polypeptide consisting of at least one of the amino acid sequences selected from the group consisting of: Sequence ID No. 3, Sequence ID No. 4, Sequence ID No. 5, and Sequence ID No. 6.

2. The polypeptide of claim 1 which includes the amino acid sequence of Sequence ID No. 5.

3. The polypeptide of claim 1 which includes the amino acid sequence of Sequence ID No. 6.

4. The polypeptide of claim 1 which includes the amino acid sequence of Sequence ID No. 5 and the amino acid sequence of Sequence ID No. 6.

5. The polypeptide of claim 4, wherein the amino acid sequence of Sequence ID No. 5 and the amino acid sequence of Sequence ID No. 6 are separated by a linker amino acid sequence.

6. The polypeptide of claim 5, wherein the linker amino acid sequence is 17 amino acids in length.

7. The polypeptide of claim 5, wherein the linker amino acid sequence is 26 amino acids in length.

* * * * *

SEQUENCE LISTING

```
<160> NUMBER OF SEQ ID NOS: 7

<210> SEQ ID NO 1
<211> LENGTH: 239
<212> TYPE: PRT
<213> ORGANISM: artificial
<220> FEATURE:
<223> OTHER INFORMATION: synthesized

<400> SEQUENCE: 1

Met Val Ser Lys Gly Glu Glu Leu Phe Thr Gly Val Val Pro Ile Leu
```

```
                1               5                      10                      15
        Val Glu Leu Asp Gly Asp Val Asn Gly His Lys Phe Ser Val Ser Gly
                        20                      25                      30

Glu Gly Glu Gly Asp Ala Thr Tyr Gly Lys Leu Thr Leu Lys Phe Ile
                        35                      40                      45

Cys Thr Thr Gly Lys Leu Pro Val Pro Trp Pro Thr Leu Val Thr Thr
                        50                      55                      60

Phe Gly Tyr Gly Leu Gln Cys Phe Ala Arg Tyr Pro Asp His Met Lys
        65                      70                      75                      80

Gln His Asp Phe Phe Lys Ser Ala Met Pro Glu Gly Tyr Val Gln Glu
                        85                      90                      95

Arg Thr Ile Phe Phe Lys Asp Asp Gly Asn Tyr Lys Thr Arg Ala Glu
                        100                     105                     110

Val Lys Phe Glu Gly Asp Thr Leu Val Asn Arg Ile Glu Leu Lys Gly
                        115                     120                     125

Ile Asp Phe Lys Glu Asp Gly Asn Ile Leu Gly His Lys Leu Glu Tyr
                        130                     135                     140

Asn Tyr Asn Ser His Asn Val Tyr Ile Met Ala Asp Lys Gln Lys Asn
        145                     150                     155                     160

Gly Ile Lys Val Asn Phe Lys Ile Arg His Asn Ile Glu Asp Gly Ser
                        165                     170                     175

Val Gln Leu Ala Asp His Tyr Gln Gln Asn Thr Pro Ile Gly Asp Gly
                        180                     185                     190

Pro Val Leu Leu Pro Asp Asn His Tyr Leu Ser Tyr Gln Ser Ala Leu
                        195                     200                     205

Ser Lys Asp Pro Asn Glu Lys Arg Asp His Met Val Leu Leu Glu Phe
        210                     215                     220

Val Thr Ala Ala Gly Ile Thr Leu Gly Met Asp Glu Leu Tyr Lys
        225                     230                     235
```

<210> SEQ ID NO 2
<211> LENGTH: 239
<212> TYPE: PRT
<213> ORGANISM: artificial
<220> FEATURE:
<223> OTHER INFORMATION: synthesized

<400> SEQUENCE: 2

```
        Met Val Ser Lys Gly Glu Glu Leu Phe Thr Gly Val Val Pro Ile Leu
        1               5                       10                      15

Val Glu Leu Asp Gly Asp Val Asn Gly His Lys Phe Ser Val Ser Gly
                        20                      25                      30

Glu Gly Glu Gly Asp Ala Thr Tyr Gly Lys Leu Thr Leu Lys Phe Ile
                        35                      40                      45

Cys Thr Thr Gly Lys Leu Pro Val Pro Trp Pro Thr Leu Val Thr Thr
                        50                      55                      60

Phe Gly Tyr Gly Leu Gln Cys Phe Ala Arg Tyr Pro Asp His Met Lys
        65                      70                      75                      80

Gln His Asp Phe Phe Lys Ser Ala Met Pro Glu Gly Tyr Val Gln Glu
                        85                      90                      95

Arg Thr Ile Phe Phe Lys Asp Asp Gly Asn Tyr Lys Thr Arg Ala Glu
                        100                     105                     110

Val Lys Phe Glu Gly Asp Thr Leu Val Asn Arg Ile Glu Leu Lys Gly
                        115                     120                     125

Ile Asp Phe Lys Glu Asp Gly Asn Ile Leu Gly His Lys Leu Glu Tyr
```

```
                130              135              140
Asn Tyr Asn Ser Gln Asn Val Tyr Leu Met Ala Asp Lys Gln Lys Asn
145                 150                 155                 160

Gly Ile Lys Ser Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 3
<211> LENGTH: 239
<212> TYPE: PRT
<213> ORGANISM: artificial
<220> FEATURE:
<223> OTHER INFORMATION: synthesized

<400> SEQUENCE: 3

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser Met Asn Val Tyr Ile Met Ala Asp Lys Gln Lys Asn
145                 150                 155                 160

Gly Ile Lys Ser Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 4
<211> LENGTH: 239
<212> TYPE: PRT
```

<213> ORGANISM: artificial
<220> FEATURE:
<223> OTHER INFORMATION: synthesized

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser Leu Asn Val Tyr Ile Met Ala Asp Lys Gln Lys Asn
145                 150                 155                 160

Gly Ile Lys Ser Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 5
<211> LENGTH: 239
<212> TYPE: PRT
<213> ORGANISM: artificial
<220> FEATURE:
<223> OTHER INFORMATION: synthesized

<400> SEQUENCE: 5

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95
```

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser Leu Asn Val Tyr Leu Met Ala Asp Lys Gln Lys Asn
145                 150                 155                 160

Gly Ile Lys Ser Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 6
<211> LENGTH: 233
<212> TYPE: PRT
<213> ORGANISM: artificial
<220> FEATURE:
<223> OTHER INFORMATION: synthesized

<400> SEQUENCE: 6

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Cys Arg Ile Lys Val Val Glu Gly
        35                  40                  45

Gly Pro Leu Pro Phe Ala Phe Asp Ile Leu Ala Thr Cys Phe Met Tyr
    50                  55                  60

Gly Ser Lys Thr Phe Val Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Pro Ser
        115                 120                 125

Asn Gly Pro Val Met Gln Lys Lys Thr Leu Gly Trp Glu Ala Ser Thr
    130                 135                 140

Glu Thr Leu Tyr Pro Ala Asp Gly Ser Leu Glu Gly Arg Asp Asp Met
145                 150                 155                 160

Ala Leu Lys Leu Val Gly Gly His Leu Ile Cys Ser Leu Lys Thr
                165                 170                 175

Thr Tyr Arg Ser Lys Lys Pro Ala Lys Asn Leu Lys Met Pro Gly Val
            180                 185                 190

Tyr Tyr Val Asp Arg Arg Leu Glu Arg Ile Lys Glu Ala Asp Lys Glu
        195                 200                 205

Thr Tyr Val Glu Gln His Glu Val Ala Val Ala Arg Tyr Cys Asp Leu
    210                 215                 220

```
Pro Ser Lys Leu Gly His Lys Leu Asn
225                 230

<210> SEQ ID NO 7
<211> LENGTH: 26
<212> TYPE: PRT
<213> ORGANISM: artificial
<220> FEATURE:
<223> OTHER INFORMATION: synthesized

<400> SEQUENCE: 7

Gly Ile Leu Asp His Ala Ser Gly Gly Gly Gly Leu Val Pro Arg
1               5                   10                  15

Gly Ser Ala Ser Gly Ala Pro Val Ala Thr
            20                  25
```